United States Patent [19]
Gershoni et al.

[11] Patent Number: 6,165,722
[45] Date of Patent: Dec. 26, 2000

[54] REPRESENTATIONS OF BIMOLECULAR INTERACTIONS

[75] Inventors: Jonathan M. Gershoni, Rehovot; David Enshel, Givatayim, both of Israel

[73] Assignee: Ramot University Authority for Applied Research & Industrial Development Ltd., Tel Aviv, Israel

[21] Appl. No.: 09/297,669

[22] PCT Filed: Nov. 4, 1997

[86] PCT No.: PCT/IL97/00354

§ 371 Date: May 6, 1999

§ 102(e) Date: May 6, 1999

[87] PCT Pub. No.: WO98/20159

PCT Pub. Date: May 14, 1998

[30] Foreign Application Priority Data

Nov. 7, 1996 [IL] Israel ........................................ 119587

[51] Int. Cl.[7] .............................. C12Q 1/70; C12Q 1/68; C12P 21/00; C12P 21/08
[52] U.S. Cl. .................................. 435/6; 435/5; 435/71.1; 530/388.3
[58] Field of Search ................................... 435/6, 5, 71.1; 530/388.3

[56] References Cited

U.S. PATENT DOCUMENTS

| | | | |
|---|---|---|---|
| 5,403,484 | 4/1995 | Ladner et al. | 435/235.1 |
| 5,516,637 | 5/1996 | Huang et al. | |
| 5,580,717 | 12/1996 | Dower et al. | |
| 5,658,727 | 8/1997 | Barbas et al. | |
| 5,925,741 | 7/1999 | Gershoni | 530/388.35 |

OTHER PUBLICATIONS

Delvin et al. "Random Peptide Libraries: A source of protein binding molecules" Science, 249:404–406, 1990.

Germino, et al. "Screening for in vivo protein–protein interactions" Pro.Natl.Acad.Sci, 90:933–937, 1993.

*Primary Examiner*—W. Gary Jones
*Assistant Examiner*—B J Forman
*Attorney, Agent, or Firm*—Mark M. Friedman

[57] ABSTRACT

A method of preparing a bimolecular interaction library for a first biological unit and for a second biological unit, each of the first and second biological units having a corresponding genetic material, the method comprising the steps of: (a) preparing a first fragment from the genetic material corresponding to the first biological unit; (b) preparing a first phage library having a first selection marker with the first fragment, such that a first peptide is displayed by the first phage library; (c) preparing a second fragment from the genetic material corresponding to the second biological unit; (d) preparing a second phage library having a second selection marker with the second fragment, such that a second peptide is displayed by the second phage library; (e) mixing the first phage library and the second phage library; and (f) co-selecting co-selected phages from the first phage library and from the second phage library by the first selection marker and the second selection marker when a selection process yields a positive result, such that the selection process yields the positive result only when the first peptide and the second peptide interact, and such that the bimolecular interaction library is formed from the co-selected phages.

34 Claims, No Drawings

REPRESENTATIONS OF BIMOLECULAR INTERACTIONS

This application is a 371 of PCT/IL97/00354 filed Nov. 4, 1997.

FIELD AND BACKGROUND OF THE INVENTION

The present invention relates to representations of bimolecular interactions and, more particularly, to the exploitation of these interactions for the production of new pharmaceuticals, such as vaccines, and diagnostic or research assays, such as antibody-based assays.

Bimolecular interactions are important for a variety of biological processes, including pathological processes. Such interactions typically involve the recognition of a three-dimensional structure, such as a protein, carbohydrate or drug ligand, by another such structure. Each of these structures is an example of a biological unit, so that such bimolecular interactions can be more generally described as an interaction between two biological units. Nature performs with ease many such interactions, which so far have proven largely refractory to analysis. Such difficulty has had a negative impact on the fields of vaccine and drug development in particular, which have had to rely on a trial-and-error approach, in the absence of defined rules for the production of novel vaccines and other pharmaceuticals. However, such trialand-error approaches are costly and inefficient. Clearly, new approaches are needed in these fields.

The problem of vaccine and drug development, which is associated with bimolecular interactions, can be narrowed to the interaction between specific epitopes on the two molecules involved. In the case of two proteins, these epitopes can be composed of particular peptides, or of peptides and carbohydrates. For a drug and its receptor, these epitopes may consist of peptides on the receptor, and functional groups on the drug. These different materials would appear to indicate that these different types of bimolecular interactions would require different systems for study. However, as described below, all of these different epitopes can be mimicked by peptides. Thus, a single system for screening large numbers of peptides could be employed to explore all of these different types of epitope interactions, since all of these interactions could be represented by different types of peptide libraries. For example, mimotopes of a carbohydrate could be found using a random peptide library, which contains all possible peptides of a given length. Alternatively, an antigen library could be used to represent peptides derived from the primary sequence of an antigen, such as a protein, for example. If such an antigen library represented all possible peptides of a given length contained within the protein, the library could be said to represent a complete pepscan of the antigen.

Such a complete pepscan could be found in a reference by Baughn et al. [Baughn, R. E., Demecs, M., Taber, L. H. and D. M. Musher, Infection and Immunity, 1996, 64:2457–2466] for the 15-kDa lipoprotein of *Treponema pallidum*, which causes syphilis. Overlapping decapeptides (ten amino acids) were synthesized, each of which overlapped the next by nine amino acids, and were offset by one amino acid, so that a complete set of decapeptides was obtained. These were then screened with sera from syphilitic rabbits in an ELISA (enzyme-linked immunosorbent assay), to find those peptides which reacted with antibodies against syphilis. The limitations to such an approach are immediately obvious, particularly since the synthesis of such a large number of peptides is both tedious and difficult to manage. Clearly, producing complete pepscans by peptide synthesis limits the approach for small proteins. Indeed, Baughn et al. note that their choice of protein was strongly influenced by size.

Thus, a new approach to the exploration of bimolecular interactions, and by extension to the fields of vaccine and drug development, is required. This approach uses combinatorial phage display peptide libraries to quickly sort through a huge number of peptides to find those peptides of interest, by a screening assay which functionally selects for a particular behavior in a peptide, as described by G. P. Smith and J. K. Scott [Scott, J. K. and G. P. Smith, Science, 1990, 249:386–390 and Smith, G. P. and J. K. Scott, Methods in Enzymol., 1993, 217:228–257]. For example, to find peptides which bind a particular protein, a phage display peptide library can be affinity-purified using that protein, and then reinfected into bacteria to make more phage containing those peptides of interest. Thus, two problems are solved simultaneously. First, a huge number of peptides can be screened in a single assay. Second, those peptides of interest can be enriched simply by infecting bacteria with the phage containing those peptides, and using the biological machinery of the bacteria to make more phages of interest. Thus, combinatorial phage display peptide libraries can do quickly and easily what artificial laboratory techniques cannot.

Such phage display peptide libraries are typically constructed in the following manner. Phages consist of DNA surrounded by coat proteins, which enable the phage to infect host bacteria and replicate themselves, producing many copies of the phage. Non-temperate phages infect the host bacteria in the following manner. First, specific coat proteins of the phage attach themselves to specific proteins on the outer cell wall of the host bacterium. Next, if the phage is a filamentous phage, the entire phage enters the host bacterium. Alternatively, if the phage is a "T" phage such as T1–T7, only the DNA of the phage enters the host bacterium. In either case, the DNA of the phage is then replicated by the genetic machinery of the host bacterium, and the coat proteins of the phage are produced by the protein synthesis machinery of the host bacterium. The coat proteins and DNA of the phage are then assembled into new phages, which accumulate and eventually burst out of the host bacterium.

To exploit this property, DNA sequences coding for the peptide of interest are inserted into the gene coding for a phage coat protein. As long as these insertions do not interfere with the life cycle of the phage, these modified phages will have coat proteins which display the foreign peptide. Filamentous phages are the preferred vectors, because two of their coat proteins can be easily modified to display foreign peptides, and thus foreign epitopes, on their surface. In general, these modifications are well tolerated. However, even if the modifications are not tolerated, the phage can still be rescued by a variety of techniques, including co-infection with a wild-type phage, known in the art as a helper phage.

The two coat proteins of the filamentous phage of types such as M13, fd and f2 are known as pIII and pVIII. There are only five copies of pIII on the phage coat, while there are about 2700 copies of pVIII on the coat. However, pIII can generally tolerate large insertions of up to a few hundred amino acids in length, while pVIII can tolerate only five or six amino acid insertions. As noted above, other techniques can be used to rescue phage with pVIII proteins containing larger insertions.

Phage replication can be controlled in the laboratory in a number of ways. For example, phages can be prepared which include a resistance gene to a particular antibiotic, which allows the host bacteria to withstand that particular antibiotic. By placing the host bacteria in growth medium which contains the particular antibiotic, those bacteria which have been infected by phages are selectively allowed to grow. Alternatively, phages can be prepared with some defect, so that only those phages which are complemented by a particular product of a phage or of a bacterium can replicate. One example of the latter is the use of helper phages to enable engineered phages to replicate, as described above.

There are two divergent methods for selecting the group of peptides which are to be inserted into the phages to form the phage library. The first type of peptide group is selected according to a known DNA or protein sequence, and forms a series of overlapping peptides, as described above for synthetic peptides. These protein-derived peptides can be used to represent a protein epitope or an entire protein. The second type of peptide group is a partial or complete set of random oligonucleotides. The first group is clearly most useful for a defined problem; for example, the mapping of a particular epitope. The second group is clearly useful when an amino acid sequence for an epitope is unknown, discontinuous in the primary amino acid sequence, or as in the case for complex carbohydrate epitopes, non-existent. In the last case, peptides, called mimotopes, have been found which mimic a selected carbohydrate epitope.

The use of each of these groups of peptides can be most easily demonstrated with reference to the field of vaccine development. Vaccinology is based upon the discovery of epitopes within the pathogen of interest which can be used to elicit an immune response which can neutralize that pathogen. Once these epitopes have been found, they can be presented to the immune system as an active vaccine, to prime the immune system against future infection, in most cases, without causing any infection or pathology themselves. Alternatively, antibodies which bind these epitopes can be isolated and administered as a passive vaccine. Thus, vaccinology depends upon the screening of large numbers of epitopes, in the hope of finding such "neutralizing epitopes", and as such is clearly amenable to the phage display library approach.

One example is the screening of random peptide phage libraries with purified antibodies or sera from humans or animals which have been challenged with a particular pathogen or with an antigen of that pathogen. For example, sera from human patients immunized against a hepatitis B viral antigen, an envelope protein from the virus, were used to screen a random library of nonapeptides (peptides of nine amino acids) inserted into the coat protein pVIII. Phages were selected which contained a nonapeptide that was both an antigenic and an immunogenic mimic of the actual viral antigen [Folgori, A. et al., EMBO, 1994, 13:2236–2243]. Such an approach has also been used in diseases where specific antigens are not known, in an effort to map those antigenic epitopes which react with antibodies in sera which have been raised against the pathogen itself.

The use of protein or antigen derived phage libraries represents a more pathogen-specific approach. The advantage of the antigen derived approach is that the peptides presented by the phage are all related to the pathogen of interest, unlike the random peptide approach, in which many of the peptides will not represent any portion of the pathogen. Thus, a higher proportion of the phages will contain peptides with potentially useful information.

An example of the use of antigen derived phage libraries to map an antigen is given by Wang et al. [Wang et al., J. Immun. Methods, 1995, 178:1–12] for the bluetongue virus outer capsid protein VP5. Bluetongue virus infects sheep and cattle. VP5 is a known antigen for this virus and is 526 amino acids in length. The VP5 gene was partially digested using DNAase I, an enzyme which cuts DNA relatively randomly. The resulting DNA fragments were sorted by size, and those of about 100–200 bp were inserted into the phage pill gene, and expressed in a phage display library. This library was screened with a monoclonal antibody to find those peptides of the VP5 protein which bind to that antibody and two different peptides were found. As estimated by the authors, this library contained about 200 different peptides, including those peptides representing the vector itself. Thus, only about 70 peptides represented the actual antigen. However, in order for every possible peptide of 30–70 amino acids contained within the VP5 protein to be represented, at least 450 different peptides would be required. Thus, this library did not even completely represent a single known antigen with overlapping peptides. A much more extensive library would be needed to represent all overlapping peptides of a given length within the antigen, thus generating a complete pepscan.

Phage libraries do not need to be used simply for mapping epitopes, however. Perham and colleagues [Greenwood, J., Willis, A. E. and R. N. Perham, J. Mol. Biol., 1991, 220:821–827; and Willis, A. E., Perham, R. N. and D. Wraith, Gene, 1993, 128:79–83] have suggested that peptide epitopes displayed by phage can act as antigens. Discrete peptides obtained from the major surface protein of the malaria parasite *Plasmodium falciparum* were injected into mice, and were successfully immunogenic, causing specific antibodies to be raised against these discrete peptides. However, the peptides used were few in number, and no suggestion was made that an entire phage library could be used as a vaccine.

An alternative to the use of phages to display peptides which correspond to inserted DNA fragments is to use the DNA fragments themselves in a DNA vaccine. DNA vaccines are, as their name suggests, composed of DNA which can stimulate antigen-specific immunity within an animal. The DNA in question must code for the antigen of interest. Such DNA vaccines include the expression library immunization system (ELI), proteins expressed in bacteria or naked DNA vaccines. As noted in Ulmer et al. [Ulmer et al., Curr. Op. Immunol., 1996, 8:531–536], naked DNA vaccines have been shown to be effective against influenza virus in animals. A particular bonus of these naked DNA vaccines is that they can elicit cellular as well as antibody responses, which many conventional vaccines cannot.

The expression library immunization system (ELI) also uses naked DNA coding for those proteins expressed by a particular pathogen, as described by Barry et al. [Barry et al., Nature, 1995, 377:632–635]. Alternatively, proteins expressed in bacteria have been used to present recombinant proteins to the immune system, as described by Mougneau et al. [Mougneau et al., Science, 1995, 268:563–566]. However, both of these methods are somewhat limited in power as compared to complete pepscans, since complete pepscans can cover substantially every possible continuous epitope of a pathogen, while these other methods only present specific proteins from a pathogen. Furthermore, as noted by Barry et al., large amounts of naked DNA were required for immunization.

Phage can also be used to present peptides for non-vaccine related interactions. Random peptide phage libraries have been used to target organs in vivo by Pasqualini and Ruoslahti [Pasqualini, R. and E. Ruoslahti, Nature, 1996, 380:364–366]. In their experiments, an entire random peptide phage library was injected into mice, and the mice were sacrificed 1–4 minutes later. Thus, although phage carrying specific peptides successfully targeted particular organs, the time frame did not permit any immunogenic effect to be observed, nor was such a potential effect even mentioned or intended by the authors.

Random peptide phage libraries have an additional advantage over more specific complete pepscans of an antigen. Random phage libraries can be used to map discontinuous epitopes, while a complete pepscan can be used to map continuous epitopes of an antigen, because of the nature of the group of peptides represented. A continuous epitope can be defined as one in which the antigenic residues reside within a short sequence of amino acids, less than from about ten to about fifteen amino acids. This sequence should definitely not be any longer than the length of the average peptide. Thus, only those epitopes which are similarly continuous will be mapped. However, many epitopes have been shown to be discontinuous. These epitopes are composed of peptides derived from different positions in the primary sequence, but which are adjacent in the three-dimensional structure of the protein. An antigen-derived peptide display library of relatively short peptides does not contain peptides which represent these epitopes.

An example of the importance of discontinuous epitopes is in the study of HIV, or human immunodeficiency virus. HIV causes almost invariably fatal disease in humans; so far, no cure or vaccine has been found. An important step in HIV infection is the binding of an HIV envelope protein, gp120, to the T-cell receptor CD4. CD4 may also be important in post-binding events in HIV infection. Indeed, it has been suggested that CD4 changes conformation in response to HIV binding, and that this altered conformation may also be responsible for post-binding infection events. Thus, the interaction of gp120 with CD4 is a natural target for vaccine design.

Part of the difficulty in finding such a vaccine, however, is that the major neutralizing epitope, the V3 region of gp120, is hypervariable, so that antibodies raised against this region tend to be specific for one type of HIV and not others. Antibodies have been found with much broader specificity, several of which clearly bind to discontinuous gp120 epitopes. Thus, such discontinuous epitopes are obvious targets for mapping, as an aid to vaccine design.

As noted above, random peptide phage libraries have been used to map discontinuous epitopes in a variety of systems. Cortese et al. [Cortese et al., Tibtech, 1994, 6:73–80] review a number of discontinuous epitopes which have been found using random peptide phage libraries. However, screening such libraries with sera has not always produced significant results, probably because of the low or incomplete representation of all discontinuous epitopes. In order to overcome this problem, a refinement of the random peptide phage library approach uses constrained peptides, in which amino acids inserted around the random peptide define a particular structure for the peptide to assume, for example a loop structure. However, this approach forces specific structures to be selected, if all random peptides are to be screened. Alternatively, the sequence of the peptide can be held constant, and those surrounding amino acids which determine the structure of the peptide can be varied. In either case, a great deal of the power of random peptide phage libraries, namely the ability to search a broad group of epitopes, is reduced. Thus, more refined discontinuous epitope mapping approaches are clearly needed, which combine the power of random peptide phage libraries with the specificity of antigen-derived phage libraries.

Carbohydrate-protein interactions have also been studied using random peptide phage libraries because of the ability of such libraries to potentially represent continuous or discontinuous epitopes of the carbohydrates themselves. These interactions are important for a number of biological processes, including lymphocyte migration and binding of the hemagglutinin protein of the human influenza virus to erythrocyte glycoproteins, an important step in infection by the virus. However, these interactions have typically been difficult to study, because of the difficulty in synthesizing complex carbohydrate ligands. To solve this problem, peptides can be found which mimic carbohydrate ligands. These peptides are also called "mimotopes" because of their mimicry of the carbohydrate epitopes. For example, Oldenburg et al. [Oldenburg et al., PNAS, 1992, 89:5393–5397] used a random octapeptide (eight amino acid) phage library and screened these phage for the ability of the peptide to bind the carbohydrate-binding protein concanavalin A. A group of peptides were found which bound to the protein, although many of these peptides had no obvious sequence homology.

There is thus a widely recognized need for, and it would be highly advantageous to have, a system for the discovery of discontinuous epitopes, to be used as vaccines, for drug design, for diagnostic purposes and for the elucidation of three-dimensional protein structure. Specifically, it would be advantageous to have a system to map discontinuous epitopes using overlapping peptides which is both complete, yet more specific than random phage libraries. It would also be advantageous to develop DNA vaccines which exploit the concept of overlapping peptides in a variety of expression systems. Finally, it would be advantageous to use discontinuous epitopes for preparing antibodies, as components of diagnostic tools, for preparing passive vaccines and for elucidating three-dimensional protein structure.

SUMMARY OF THE INVENTION

According to the present invention there is provided a method of preparing a bimolecular interaction library for a first biological unit and for a second biological unit, each of the first and second biological units having corresponding a genetic material, the method including the steps of: (a) preparing a first fragment from the genetic material corresponding to the first biological unit; (b) preparing a first phage library having a first selection marker with the first fragment, such that a first peptide is displayed by the first phage library; (c) preparing a second fragment from the genetic material corresponding to the second biological unit; (d) preparing a second phage library having a second selection marker with the second fragment, such that a second peptide is displayed by the second phage library; (e) mixing the first phage library and the second phage library; and (f) co-selecting the first phage library and the second phage library by the first selection marker and the second selection marker by a selection process, such that the selection process yields a positive result substantially only when the first peptide and the second peptide interact, such that co-selected phages from the first phage library and co-selected phages from the second phage library form the bimolecular interaction library only when the selection process gives the positive result.

Preferably, the first and the second fragment can be prepared in one of the following ways. According to the first method, the first fragment is prepared by at least partially digesting the genetic material corresponding to the first biological unit and the second fragment is prepared by at least partially digesting the genetic material corresponding to the second biological unit. According to the second method, the first fragment is prepared by: (a) at least partially digesting the genetic material corresponding to the first biological unit to form a plurality of fragments; (b) ligating the fragments to form at least one ligated fragment; and (c) at least partially digesting the ligated fragment; and the second fragment is prepared by: (d) at least partially digesting the genetic material corresponding to the second biological unit to form a plurality of fragments; (e) ligating the fragments to form at least one ligated fragment; and (f) at least partially digesting the ligated fragment. According to the third method, the first fragment is prepared by: (a) at least partially digesting the genetic material corresponding to the first biological unit to form a plurality of fragments; (b) ligating the fragments to form at least one ligated fragment; and (c) at least partially digesting the ligated fragment; and the second fragment is prepared by: (d) at least partially digesting the genetic material corresponding to the second biological unit. Optionally, either the first or the second fragment, or both, can be prepared from the intact genetic material corresponding to the first or second biological units, respectively.

Preferably, the first selection marker is an antibiotic-resistance gene, and the second selection marker is infectivity. Alternatively and preferably, the first selection marker is a first fluorescent dye having a first emission spectrum, and the second selection marker is a second fluorescent dye having a second emission spectrum, the first and second spectra combining to form a third emission spectrum. Also alternatively and preferably, the first selection marker is the first peptide and the second selection marker is the second peptide, such that the phages co-selected from the first library and the phages co-selected from the second library collectively have a characteristic selected from the group consisting of density, size and charge.

According to further features in preferred embodiments of the invention described below, there is provided a method for obtaining a bimolecular interaction combination of a first biological unit and of a second biological unit, each of the first and the second biological units having corresponding genetic material, the method including the steps of: (a) preparing a bimolecular interaction library for the first biological unit and the second biological unit according to the above method; and (b) obtaining a first peptidic unit of the first peptide and a second peptidic unit of the second peptide, the first peptidic unit and the second peptidic unit forming the bimolecular interaction combination. Preferably, the peptidic unit is the peptide. Alternatively and preferably, the peptidic unit is a DNA fragment coding for the peptide.

According to another embodiment, there is provided a method for obtaining a representation of a first biological unit capable of interacting with a second biological unit, each of the first and the portion of the second biological units having corresponding genetic material, the method including the steps of: (a) preparing a bimolecular interaction combination according to the above method; and (b) obtaining the peptidic unit of the first peptide from the bimolecular interaction combination, the peptidic unit forming the representation of the first biological unit.

In the following methods, most of the examples will use DNA, rather than RNA, as the genetic material. It will be appreciated, however, that many of these methods could also be used for RNA, so that the use of the term "DNA" is not intended to be limiting in these examples. The term "genome" is hereinafter defined as the complete genetic material of an organism, whether that genetic material is DNA or RNA based.

DESCRIPTION OF THE PREFERRED EMBODIMENTS

The present invention is of both methods and compositions which can be used to analyze and control bimolecular interactions. Specifically, the present invention includes libraries for bimolecular interactions, which are the basis for a number of products and methods, including both passive and active vaccines and diagnostic and research assays. Further examples include, but are not limited to, the discovery of lead molecules for drug design, receptor modulators, antidotes, inhibitors and molecular decoys.

The invention is illustrated by the following examples, which describe the construction of bimolecular interaction libraries, as well as methods and compositions which use these libraries.

Please note that many experimental protocols, which are well known in the art, are used in the following descriptions but are not described in detail. These prior art protocols are described in a number of textbooks and protocol books. One example of such a book is *Molecular Cloning* by J. Sambrook et al., Cold Spring Harbor Laboratory Press, 1989, which is incorporated by reference as if fully set forth herein for the sole purpose of providing complete descriptions of well known prior art experimental protocols. A further example is *Cell Biology* ed. by J. E. Celis, Academic Press Inc., 1994.

EXAMPLE 1

Methods of Constructing a Bimolecular Interaction Library

As described in the Background section above, bimolecular interactions between two single biological units are important in the fields of drug and vaccine development, yet have proved largely refractory to analysis. As defined herein, the term "single biological unit" refers to a unit with a discrete biological function. Examples of such biological units include, but are not limited to, a protein, two or more proteins which transiently interact, such as gp120 and CD4, a group of proteins such as a cytoskeleton or those proteins coded for by an entire genome of an organism such as HIV, and non-protein structures which can be mimicked by a mimotope, or a portion of any of these examples. Mimotopes can mimic natural structures such as a tRNA, ribozymes and carbohydrates, or artificial structures such as man-made chemicals.

Recently, pepscans have been used to study bimolecular interactions between two proteins or fragments of proteins, as noted in the Background above. Pepscans include peptide fragments of a protein or protein(s) of interest. In a complete pepscan, these peptides overlap such that each peptide is offset from the next by one amino acid residue. However, a pepscan does not need to be limited to a single protein or even a group of proteins. Instead, a pepscan can also be constructed for a single biological unit, as described below. Furthermore, a discontinuous library can be constructed for a single biological unit, as described below, which has the advantage of being able to present discontinuous epitopes, unlike the pepscan which can only present continuous epitopes. As noted above, a continuous epitope can be defined as one in which the antigenic residues reside within a short sequence of amino acids, less than from about ten to about fifteen amino acids. This sequence should definitely not be any longer than the length of the average peptide. A discontinuous epitope, however, includes the novel contiguous presentation of two different amino acid sequences which were previously discontinuous in the original primary amino acid sequence.

Once the pepscan or discontinuous library has been constructed for the single biological unit of interest, a phage display library can then be used to quickly sort through a huge number of peptides to find those peptides of interest, by a screening assay which functionally selects for a particular behavior in a peptide.

Typically, such screening methods have used antibodies which bind peptides of interest. Yet the phage display library method can also be adapted to select for peptides on the basis of their bimolecular interaction, which more closely approximates the original bimolecular interactions between the two biological units of interest. Since, as noted above, the biological unit can be any biological unit which can be mimicked by a peptide, these interactions can also involve a mimotope. Mimotopes are peptides which can mimic a selected carbohydrate epitope for example, as described in the Background section. Thus, any of the single biological structures described above can be approximated by a peptide or peptides.

Studying the bimolecular interactions between the biological units by using peptides requires a bimolecular interaction library. Such a library can be constructed as follows. First, a fragment of the genetic material which corresponds to each single biological unit is prepared. Note that for convenience, the two biological units are referred to as the "first biological unit" and the "second biological unit", although in fact these two units are interchangeable. It should be noted that since a fragment is prepared for each single biological unit, ultimately a plurality of fragments is prepared, at least one fragment for each unit. However, for clarity, the method given below refers to only "a fragment". The term "a fragment" is used to mean at least one fragment. If only one fragment is desired, then substantially the entirety of the genetic material can be used as the "fragment", in which case it can be processed as described below for the post-digest fragments. For example, if the interaction between two whole proteins was to be studied, each fragment could be a gene coding for one of the proteins. By the term "corresponds" it is meant that the genetic material codes for the peptide or peptides which represent the single biological unit.

Alternatively, and preferably, if multiple fragments are desired, then a digest of the genetic material is required. The digest, which is either partial or complete, is prepared by digesting the genetic material so that it is cut into fragments as described hereinbelow.

The digest of the genetic material is preferably substantially complete, such that DNA fragments initiate at substantially every possible base pair. The term "complete digest" is hereinafter defined as a digest in which DNA fragments initiate at substantially every possible base pair. Alternatively, it can be a partial digest, such that DNA fragments initiate at a subset of every possible base pair. In either case, an enzyme can be used to perform the digest. For a substantially complete digest of the DNA, the enzyme DNAase I is often used. DNAase I cuts DNA relatively randomly; that is, it cuts between any two bases with relatively equal efficiency. When DNAase I is incubated with DNA under appropriate conditions, a collection of fragments of different sizes is obtained which initiate at substantially every single possible base pair. Thus, the genetic material is covered by DNA fragments which are offset by one base pair. Appropriate conditions are chosen so that a significant fraction of the fragments fall within a desired size range. This collection of fragments is a substantially complete digest of the genetic material corresponding to the single biological unit.

For a partial digest, enzymes with greater specificity can be used, under appropriate conditions for activity of the enzyme. For example, the enzyme EcoRI recognizes the following sequence:

```
          123456
        1 GAATTC
        2 CTTAAG
```

EcoRI then cuts between G and A on strand 1 (bases 1 and 2), and between A and G on strand 2 (bases 5 and 6). Preferably, enzymes which cut more frequently, such as SauIIIA, are used. SauIIIA recognizes a four-base sequence and so is more likely to encounter the appropriate sequence on the DNA. Alternatively, a combination of such enzymes is used. DNAase I can also be used under appropriate conditions such that the DNA is only partially digested, for example by limiting the amount of time that DNAase I is allowed to cleave the DNA or by limiting the concentration of enzyme, or by limiting both of these factors.

Optionally, either a substantially complete or a partial digest could be prepared by mechanical shearing of the DNA. Such mechanical shearing is well known in the art, and can be accomplished by sonication of the DNA, for example. Mechanical shearing has the further advantage of producing fragments of a more homogeneous size, since shearing forces are greatest in the middle of molecules rather than the edges, and larger molecules are more susceptible to shearing than smaller molecules. One disadvantage of sonication is that the temperature can become very high where the ultrasound waves enter the solution, potentially damaging the DNA.

Optionally, the group of fragments can be further processed in order to represent discontinuous epitopes. As described in the Background section above, a peptide representing a single biological unit, and hence both a "fragment" of substantially the entirety of the genetic material corresponding to a single biological unit and fragments from a digest, can only be used to represent a continuous epitope or epitopes. However, many epitopes are discontinuous epitopes, as described in the Background section above. In order to represent these epitopes, the group of fragments from the digest must be prepared as follows.

First, at least two of the DNA fragments from the digest are ligated together under appropriate conditions according to methods which are well known in the art. This ligation results in at least one ligation product, which is simply at least one DNA segment formed by ligating the at least two DNA fragments from the digest. Preferably, appropriate conditions are used for ligation so that more than two of the fragments ligate per a ligation product.

The ligation product is then digested again to form DNA fragments, which are then sorted by size to separate those fragments which fall within the desired size range. Preferably this size range is larger than the size range from the first digest. Similarly to the first digest, this second digest can either be partial or substantially complete, and can be performed according to a variety of methods, including but not limited to, enzymatic and mechanical. If a substantially complete digest is desired, DNAase I can be used, by incubating the ligation product with DNAase I under appropriate conditions, in order to obtain at least one DNA fragment. If a partial digest is desired, again enzymes such as EcoRI, SauIIIA or even DNAase I can be used under the appropriate conditions, as described above. Alternatively, mechanical shearing can be used, by sonication of the ligation product for example. In any case, if desired, DNA fragments which fall within a desired size range can be separated trom the rest of the digest. Each of these fragments is a "conformational fragment"; that is, a fragment which codes for a peptide which is potentially capable of representing a discontinuous epitope.

After either the digest, either partial or substantially complete, has been prepared, and/or optionally after the ligation and second digest has been prepared, the resulting fragments are processed so that these fragments have blunt ends, if a blunt-ended vector is used (see below), by enzymatic degradation or synthesis for example. If substantially the entirety of genetic material is used as a "fragment", then it also must be processed so that it has blunt ends if a blunt-ended vector is used. If a digest has been prepared, then those fragments which fall within a desired size range are then separated from the collection of fragments. For example, fragments of from about 50 bp to about 150 bp can be separated by size fractionation. Since only a portion of the collection of fragments from the digest fall within the desired size range, the rest of the fragments are not further used, so a larger quantity of starting genetic material is required to obtain a sufficient quantity of fragments of the desired size range.

Next, after the fragment or group of fragments have been prepared, each phage library is prepared to receive the fragment or group of fragments. As noted above, since two biological units are being represented, each biological unit requires its own phage library, so that there are two phage libraries. Such a phage library includes at least one, and preferably a plurality of phages. The phage library is prepared by modifying a gene of the phage, so that each fragment can be cloned into the phage gene. The product of that gene, a chimeric phage protein, will then include a foreign peptide. The sequence of the foreign peptide will depend upon the inserted DNA fragment. Preferably, a gene for a coat protein is used, so that the phage will display the foreign peptide on its outer surface. Typically, filamentous phages are used because they have coat proteins which are easily modified to receive the foreign DNA fragment. The preferred coat proteins are pIII and pVIII. pIII can tolerate insertions of foreign peptides of up to a few hundred amino acids in length, but only five copies of pIII are on the phage coat. About 2700 copies of pVIII are on the phage coat, but pVIII can only tolerate insertions of up to about five or six amino acids, unless special rescue methods are used, as described in the Background section above. The choice of a particular coat protein depends upon both the length of the foreign peptide and upon the desired number of copies per phage of the foreign peptide.

Once the particular coat protein has been chosen, the gene is modified to contain a unique blunt end restriction site, preferably at its N terminal region, using methods which are well known in the art. The particular nature of the restriction site depends upon the strain of phage which is used. For example, for the pIII construct of the fUSE5 vector of the filamentous phage fd-tet such a site could be inserted between the two Sfi-1 sites present on the vector [Scott, J. K. and G. P. Smith, Science, 1990, 249:386–390 and Smith, G. P. and J. K. Scott, Methods in Enzymol., 1993, 217:228–257]. However, it is possible to construct many such blunt-ended phage vectors, by manipulating restriction sites so that DNA fragments can be inserted where desired. Alternatively, oligonucleotide linkers can be used to clone the DNA fragments in distinct and unique restriction sites in the vector which are not necessarily blunt-ended.

Finally, the "fragment" of substantially the entirety of the genetic material, or alternatively selected fragments from the digest of the genetic material, or alternatively a conformational fragment or fragments, are cloned into the appropriately cut phage vector, using methods which are well known in the art. These phages constitute the phage library. Such a phage library can accommodate up to from about $10^9$ to about $10^{10}$ phages, and can therefore accommodate even a complete pepscan of the entire genome of an organism.

As an example, consider the production of a complete pepscan of the entire HIV (Human Immunodeficiency Virus) genome, which is about 9000 bp. About 3000 peptides of a desired size range would be required in order to have a peptide starting at substantially every possible residue. However, since only one of eighteen, or about five percent of the inserted DNA fragments can express a functionally relevant peptide, in order to fully represent 3000 peptides for about one-fold coverage, a library of about 60,000 phages is required, of which only about 3000 phages will be viable. Libraries of up to from about $10^9$ to about $10^{10}$ phages can easily be prepared. Thus, a complete pepscan of the entire genome of HIV can easily be accommodated within such a library.

In order to prepare the phage display library for a complete pepscan of the HIV genome, a substantially complete digest of the HIV genome would need to be prepared, as described above. Since HIV is a retrovirus, the complete HIV RNA would need to be reverse-transcribed into DNA. This DNA would then need to be substantially completely digested as this term is defined above and fragments of the desired size range separated. For example, the DNA could be incubated with DNAase I under appropriate conditions and fragments of from about 75 to about 150 bp could be separated. These fragments would then be cloned into a coat protein gene of an appropriately cut filamentous phage vector, for example the pIII gene of the fUSE5 vector, or a pVIII vector used in conjunction with a helper phage or other method to produce hybrid phages [Greenwood, J., Willis, A. E. and R. N. Perham, J. Mol. Biol., 1991, 220:821–827; and Willis, A. E., Perham, R. N. and D. Wraith, Gene, 1993, 128:79–83]. Now the complete pepscan of the HIV genome is in a phage display library.

Further examples of phage display libraries containing a complete pepscan of the genome of an organism can also be given. For example, the typical bacterial genome is about one million bp, or $10^6$ bp. About $3*10^5$ peptides of the desired size range would therefore be necessary, so that a library of about $6*10^6$ phage would be required for one-fold coverage, of which about five percent would be viable. Such a library could be prepared for *Mycobacterium tuberculosis*, a bacteria which was previously described in the Background section above, by using the above methods. Alternatively, libraries could be prepared for any bacterium, preferably pathogenic bacterium.

Other examples of organisms include yeast, which has a genome of about $10^7$ bp. A library of about $6*10^7$ phage would be required for a complete pepscan of the yeast genome. As noted above, the preparation of such a library would involve the substantially complete digestion of the yeast genome, and separating DNA fragments of the desired size. These fragments would then be cloned into the desired phage gene, to form the phage display library.

Still other examples of organisms for which such phage display libraries can be constructed include parasites, which typically have genomes of about 100 million bp, or $10^8$ bp, as described above. Examples of such parasites are those which cause leishmaniasis, including *Leishmania major* and

*L. braziliensis braziliensis.* Another example of a parasite is *Plasmodium falciparum,* which causes malaria. A phage library of a complete pepscan of any one of these parasites could be prepared as described above.

Clearly, a phage display library could be prepared for a number of organisms including, but not limited to viruses including but not limited to retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis,* salmonella, staphylococcus species such as *Staph. aureus,* and shigella; parasites including, but not limited to, plasmodium species such as *Plasmodium falciparum,* leishmania species such as *Leishmania major* and *L. braziliensis braziliensis,* entamoeba species, giardia species, trichomonas species and trypanosoma species; and yeasts including, but not limited to, *Candida albicans.*

The number of phages which are required for a substantially complete representation of a single biological unit with conformational fragments depend upon a number of factors, such as the type of display carrier, the number of DNA basepairs required to represent the single biological unit, the size of fragments desired from both digests, the extent of both digests and the extent of ligation. However, since even a genome can be accommodated by a phage library, clearly a smaller single biological unit, such as a single protein for example, could be accommodated by a phage library.

Since there are two biological units, as noted above there must be two phage libraries, one for each biological unit. Thus, the first phage library is for the first biological unit, and the second phage library is for the second biological unit. Once the phage libraries have been prepared for each single biological unit, both the first phage library and the second phage library are mixed. During this mixing, the first and second peptides which are displayed on the coat of the phages in the first and second phage libraries, respectively, are allowed to interact. In order for such interaction to be successful, the phages must have undergone at least one replication cycle, so that the new peptides coded for by the inserted DNA fragments can be displayed on the coat proteins of the phages. If the first and second peptides do interact, then the phages displaying these peptides can be described as joined, or physically interlinked. These two joined phages can then be distinguished from the other single phages by a suitable selection procedure.

In order for such a selection procedure to be successful, in addition to a fragment from the genetic material of each single biological unit, each phage library must contain a different selection marker. These selection markers enable the phage libraries to be distinguished from each other and from wild type phages. Examples of selection markers include fluorescent dyes, ability to replicate under particular environmental constraints, and even the first and second peptides themselves.

As a first example, the first selection marker could be a first fluorescent dye having a first emission spectrum, and the second selection marker could be a second fluorescent dye having a second emission spectrum. Such dyes could be attached to phages directly, for example by partially substituting amino acids, modified to have a particular dye attached thereto, during synthesis of the coat proteins. Alternatively, another coat protein, different from the protein which contains one of the peptides of interest, could be modified to include a particular epitope. An antibody which binds that epitope could then have a dye molecule attached thereto, so that the antibody would bind to a phage displaying that epitope and the dye molecule would act as a marker.

In either case, the phages which were joined by the interaction of the first and second peptides could be selected as follows. When these two fluorescent dyes are placed in relatively close proximity, as by the phages having the respective dyes being joined by the interactions of the first and second peptides, a third spectrum could be produced. This third spectrum could be formed in one of two ways. First, the first and second spectra could simply combine. An example would be placing a rhodamine molecule on one phage, either directly or indirectly, and a fluorescein molecule on the other. Rhodamine emits light which is red in appearance, and fluorescein emits light which is green in appearance, so that the spectra of both dye molecules would appear substantially yellow when combined. The second method would require the two fluorescent dye molecules to be in such close proximity that excitation of the first dye molecule causes the second dye molecule to fluoresce due to energy transfer, producing light of a third spectrum.

As a second example of such markers, the first and second markers could permit their respective phages to replicate under particular environmental constraints only when these phages are joined. Thus, each marker would have to permit the phage to replicate under a different constraint. For example, the first phage could include an antibiotic resistance gene, which would transfer resistance to a particular antibiotic to the host bacterium. However, this phage would also be defective in infectious ability. The second phage would be able to infect the host bacterium, but would not confer antibiotic resistance. Thus, the second phage would help the first phage infect the host bacterium by co-infection substantially only when the first and second peptides interact.

Optionally, the first phage can be made defective in infectious ability by modifying the pIII gene so that pIII was no longer able to participate in the process of infection. Such an insertion would prevent the phage from effectively infecting the host bacterium. Alternatively and preferably, the species specificity of the first phage could prevent the first phage from infecting the host bacterium, while the species specificity of the second phage would permit the second phage to infect the host bacterium. Species specificity refers to the ability of a phage to infect a particular strain or species of bacteria. Thus, certain types of phage can only infect certain strains or species of bacteria. Optionally, a strain of bacteria could be engineered by altering specific components of the cell wall of the bacteria, such that the first phage is unable to infect the strain, but the second phage is able to infect. One advantage of using species specificity is that the first, or "non-infective" phage, is non-infective with respect to the bacterial strain or species used for co-selection. However, the first phage could still be grown using a compatible host before co-selection.

In either case, the interaction of the first and second peptides causes the first and second phages to be joined, or physically linked. The second phage, which is able to infect, then helps the first phage to infect the cell, preferably by promoting entry of the first phage. This does not exclude the possibility of using other phages, such as T phages, which inject their DNA into the host bacterium. Optionally, even mixtures of filamentous and injecting phages could be used.

After co-infection, the host bacterium is challenged with an antibiotic, resistance to which would be coded for by the antibiotic resistance gene of the first phage. Thus, the first phage would enable the bacterium to grow, permitting both phages to replicate. These phages could only be deficient in the infection part of the cycle, rather than in replication or lysis, to permit the initial assembly of complete phages, and to enable the second phage to co-infect bacteria with the first phage for selection by both markers.

As noted above, both phages need to be displaying their respective peptides on their coat proteins in order for such a selection process to operate. However, this presents a problem for the first phage, which must be deficient in infectious ability. Electroporation can be used to introduce such a phage into the host bacterium, so that complete phages with assembled coat proteins can be produced. Finally, the first and second phages are mixed, as described above.

As a third example, the first and second selection markers could be the first and second peptides, so that the selection process would differentiate between single phages and joined phages. Such differentiation could be by size, density or charge. Two joined phages, held together by the interactions of their respective peptides, would clearly be larger than a single phage, both in terms of geometric volume and molecular weight. Methods such as size fractionation, for example, could exploit this size difference to separate joined phages from single phages. Alternatively, two joined phages could have a different density than a single phage. Finally, the overall charge of two joined phages could be different than that of a single phage. Any of these methods could therefore be used to separate joined phages from single phages, thereby distinguishing between peptides which interact and those which do not.

Thus, it is important that the first phage library and second phage library are co-selected by the first selection marker and the second selection marker by a selection process, such that the selection process give a positive result substantially only when the first peptide and the second peptide interact, such that co-selected phages from said first phage library and co-selected phages from said second phage library form the bimolecular interaction library only when said selection process gives the positive result.

EXAMPLE 2

Methods of Constructing a Bimolecular Interaction Combination

As described in Example 1, a bimolecular interaction library can be constructed for two biological units. Once the library has been prepared, a bimolecular interaction combination can be prepared. The bimolecular interaction combination can be used to analyze the interaction between the two biological units and is prepared as follows.

First, a bimolecular interaction library is prepared for a first and a second biological unit according to any of the methods in Example 1. This library includes phages which display interacting peptides, which represent the interacting components of the two biological units. Next, a first peptidic unit of the first peptide and a second peptidic unit of the second peptide are obtained. These two peptidic units form the bimolecular interaction combination.

As defined herein, a "peptidic unit" can be one of the two interacting peptides. Alternatively, the peptidic unit can be the DNA fragment which codes for one of the two interacting peptides. In either case, the bimolecular interaction combination directly or indirectly represents the components of the two biological units which interact.

EXAMPLE 3

Methods of Constructing a Representation of a Biological Unit Capable of a Bimolecular Interaction As noted above in Example 2, a bimolecular interaction combination can be prepared from two biological units which are capable of interacting. This combination directly or indirectly represents the components of the two biological units which interact. However, it may be desirable to isolate the component or components of one of the biological units which interact with the second biological unit. For example, if one of the biological units is an HIV envelope protein, such as gp120, and the second biological unit is the CD4 protein, then isolating the portion or portions of gp120 which interact with CD4 could result in the development of new pharmaceutics. Such isolation is possible by using a representation of the biological unit.

A representation of a first biological unit which is capable of interacting with a second biological unit is prepared as follows. First, a bimolecular interaction combination of the first and second biological units is prepared according to one of the methods in Example 2, so that the interactions of the first and second biological units are mimicked by the first and second peptides of the first and second phage libraries. Next, the peptidic unit of the first peptide is obtained from the bimolecular interaction combination. This peptidic unit, which as defined in Example 2 can be either the first peptide itself or the DNA fragment which codes for the first peptide, forms the representation of the first biological unit. Thus, this representation either directly or indirectly represents at least one of the components of the first biological unit which interact with the second biological unit.

Examples of potential uses for such a representation include, but are not limited to, an inhibitor of a reaction, as a molecular decoy, as a pharmaceutical treatment, as a lead molecule for drug design and as a receptor modulator. For example, a representation of CD4 could bind gp120, and effectively prevent gp120 from binding to an actual CD4 protein, thus preventing infection. Alternatively, a representation of a receptor which interacts with a particular toxin could be given as an antidote, as this representation could intercept and bind the toxin before the toxin could bind to the receptor itself.

EXAMPLE 4

Methods of Preparing and Administering an Active Vaccine Against a Biological Unit As noted above in Example 3, a representation of at least one of the components of a first biological unit which interact with a second biological unit can be prepared. Such a representation could be useful for the development of new therapeutics, if for example the first biological unit was an HIV envelope protein such as gp120, and the second biological unit was a human immune cell membrane protein such as CD4. One example of such a therapeutic is an active vaccine.

As described in the Background section above, an active vaccine causes at least one epitope of a first biological unit to be presented to the immune system of an organism, which is the organism to be vaccinated. The first biological unit is typically, but not necessarily, a pathogenic organism, such as a virus, bacterium, yeast or parasite. The first biological unit could also be a toxic substance, such as a snake, insect or spider venom toxin, a plant toxin or even a synthetic toxin. Alternatively, the first biological unit could even be a part of the organism to be vaccinated, such as a cancer cell, or a portion thereof, for example. It should be noted, however, that in the case of autoimmune reactions, treatment of cancerous cells, or cells exhibiting inappropriate activity for the stage in the life cycle of the organism, the first and second organisms are effectively the same organism. Thus, the "epitope of the first organism" is actually an epitope expressed by a cancerous cell or a cell exhibiting inappropriate activity for the stage in the life cycle of the organism. Alternatively, in the case of autoimmune reactions such as myasthenia gravis, lupus erythematosus or rheumatoid arthritis, the "epitope of the first organism" is normally expressed, but the immune reaction is inappropriate. In any case, the terms "first" and "second" organism are used below for clarity, it being understood that the "first" and "second" organisms can be the same organism.

For any of these cases, the second biological unit would include at least one component which interacts with the first biological unit. Such a component could be a protein from an organism which is attacked by a pathogenic organism, for example. The only requirement placed on the first and second biological units is that they must have corresponding genetic material, which could be obtained by the use of mimotopes, as described in Example 1 above. One advantage of selecting an epitope of a first biological unit which is capable of interacting with a second biological unit is that these epitopes are less likely to mutate, and are more likely to be commonly presented across species or types of organisms, because such epitopes are functionally necessary. For example, an epitope of gp120 which interacts with CD4 is less likely to mutate than a non-interacting epitope.

An active vaccine against a first biological unit, which is capable of interacting with a second biological unit, could be prepared as follows. First, a representation of the first biological unit could be prepared according to the methods of Example 3. Next, a vaccine carrier could be provided for the representation. The vaccine carrier is a pharmaceutical composition, which may include thickeners, carriers, buffers, diluents, surface active agents, preservatives, and the like, all as well known in the art. Pharmaceutical compositions may also include one or more active ingredients such as but not limited to immune-system stimulating agents, known in the art as adjuvants, and the like in addition to the representation. For example, the vaccine carrier can include pharmaceutically appropriate buffers.

If the representation was a DNA fragment, the vaccine carrier could include one of the following components. For example, the vaccine carrier can include a plurality of phages which present the peptide coded for by the DNA fragment. Preferably these phages are filamentous phages. Most preferably, the DNA fragment is inserted into a coat protein of the phage, optionally pIII or pVIII. In this case an adjuvant is not required as the phages themselves act as immune system stimulants.

Optionally, the DNA fragment could be inserted into genetic material of the bacteria, so that the peptide can be produced by a plurality of bacteria which synthesize the peptide. Since bacteria themselves are both highly immunogenic, as well as potentially hazardous to administer directly to the organism to be immunized, substantially only the synthesized peptide should be included in the vaccine carrier. Preferably the peptide is cloned as a conjugate to a secreted bacterial protein, to facilitate purification. These conjugates are then collected from the bacterial growth media and purified from other media constituents. Proper selection of the bacterial protein can eliminate the need for an adjuvant, as the bacterial protein itself can act as the adjuvant.

The insertion of the DNA fragment into the genetic material of the bacteria could be performed as follows. First, the fragment can be cloned into a vector, such as a phage, a plasmid, a phagmid or a cosmid. Examples of commercially available prokaryotic vectors include pKK223-3 and pTrc99, both available from Pharmacia Biotech. Such vectors are well known in the art. Although a phage can act as a vector, the phage itself does not display the corresponding peptide on its outer coat. Similarly, the other vectors are used only to introduce DNA fragments into the bacteria, but are not themselves used to display the foreign peptide.

Next, the vector, with the inserted fragment, is transfected into the bacterial strain of choice. Again, transfection procedures are well known in the art. These bacteria then produce the peptide coded for by the fragment. These peptides can accumulate within the cell. Alternatively, they can be displayed on the cell wall of the bacteria, for those bacteria which display proteins or peptides on their cell wall. Alternatively and preferably, they can be secreted into the bacterial growth media, from which they can be collected.

Also optionally, the vaccine carrier can include the eukaryotic expression vector itself, so that the DNA fragment is inserted into the vector by cloning the DNA fragment into a eukaryotic expression vector. Both such vectors and such methods are well known in the art. For example, commercially available vectors include pSVK 3 and pBPV, both available from Pharmacia Biotech. The eukaryotic expression vector itself is then placed in the vaccine carrier. The combination of the eukaryotic expression vector and the vaccine carrier is an example of a "naked DNA vaccine", as described in the Background above.

Once the vaccine has been prepared according to one of the above methods, it can be administered to an organism in a number of ways, which are well known in the art. For example, administration may be done topically (including ophtalmically, vaginally, rectally, intranasally), orally, by inhalation, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on responsiveness of the immune system of the organism to be vaccinated, but will normally be an initial dose of the vaccine. If necessary a booster dose or doses can be administered at a later date to achieve a desired level of protection against the first organism, as measured by antibody titer, for example. Persons of ordinary skill in the art can easily determine optimum dosages, dosing methodologies and repetition rates.

Examples of organisms to which such a vaccine could be administered include, but are not limited to, humans, pets such as dogs and cats, farm animals such as horses, pigs, sheep, cattle (both beef and dairy) and goats, laboratory animals such as mice, rats, monkeys and rabbits, and wild animals in captivity such as elephants, lions, tigers and bears, and other mammals, fish including, but not limited to, trout, salmon, carp and tuna, and birds, including, but not limited to, poultry such as chickens and turkeys, ducks and geese.

EXAMPLE 5

Methods of Detecting and Obtaining an Antibody Against an Epitope of a Biological Unit As noted above in the Background section, an epitope of a first biological unit can be bound by antibodies which are produced by the immune system of an organism to be vaccinated. Methods of detecting antibodies which bind continuous epitopes are well known in the art, and generally involve screening immune material which contains at least one antibody.

The immune material which is screened can be prepared by administering a vaccination entity to the organism to be vaccinated. The vaccination entity can include either the first biological unit, or a representation of the first biological unit. The representation of the first biological unit can be prepared according to one of the methods of Example 3. Each of these methods results in the preparation of either a peptide, or of a DNA fragment which is presented by a display carrier, which can also be an expression carrier. The display carrier can be a phage display library, bacterial expression library or an eukaryotic expression library, depending upon the method which is used.

Optionally, the immune material which is screened can include serum with at least one antibody. For example, such serum could be obtained from a human patient who has been challenged with the first biological unit. Alternatively, such serum could be obtained from an animal, including, but not limited to, a rabbit, a horse or a mouse, which has been challenged with the first biological unit.

Also optionally, the immune material can include polyclonal antibodies. Polyclonal antibodies can be prepared by injecting a rabbit, for example, with a substance or substances which provoke an immune response. For commercial purposes, a mammal with a larger blood volume can be used, such as a horse for example. Such substances can include the first biological unit. The rabbit then produces polyclonal antibodies in response to these substances. Such antibodies are called "polyclonal" because they are derived from more than one B-cell clone.

Monoclonal antibodies, on the other hand, bind to only one epitope of the first biological unit. Monoclonal antibodies are obtained from hybridomas, which are produced by fusing spleen-derived B cells which secrete a single antibody, with immortal myeloma cells. Such cells can be prepared from mice cells, for example, or by immortalization of human B-cells by EBV (Epstein-Barr virus), for example.

Once the immune material has been prepared, similar methods to those well known in the art can be used to detect antibodies which bind an epitope, either discontinuous or continuous, of the first biological unit. As a first step, a screening entity is prepared. This screening entity can include either the first biological unit, or a representation of the first biological unit, such that the vaccination entity and the screening entity are not identical. The representation of the first biological unit can be prepared according to one of the methods of Example 3. Each of these methods results in the preparation of either a peptide, or of a DNA fragment which is presented by a display carrier, which can be a phage display library, a bacterial expression library or an eukaryotic expression library, depending upon the method which is used. Alternatively, the screening entity can include at least a portion of the first biological unit of interest.

After the screening entity has been chosen, it is screened with immune material which contains at least one antibody. Such screening can be performed in a number of different ways which are well known in the art, and some of which are described in *Molecular Biology of the Cell*.

For example, the screening entity can be substantially immobilized on a solid support. Examples of such solid supports include, but are not limited to, porous membranes such as nylon and nitrocellulose, non-porous films such as polypropylene, or plastics. The immune material can then be incubated with the screening entity under appropriate conditions, so that any antibody or antibodies can bind to the appropriate epitope or epitopes, as presented by the screening library [Smith, G. P. and J. K. Scott, Methods in Enzymol., 1993, 217:228–257].

Finally, the presence of the bound antibody or antibodies can be detected in a variety of ways, which are well known in the art. For example, the antibody or antibodies can be directly labelled with a substance which acts as a marker for the presence of the antibody or antibodies. Examples of such substances include, but are not limited to, fluorescent dyes or radioactive substances. Alternatively, greater sensitivity can be obtained by using a secondary antibody which can bind to a variety of antibodies. The secondary antibody can be labelled as above. Optionally, an ELISA (enzyme-linked immunoassay) can be used, in which an enzyme, such as alkaline phosphatase, is linked to the secondary antibody. A substrate is incubated with the enzyme, and a sensitive chemical test is used to detect the presence of the enzymatic product.

Once the antibody has been detected, the antibody can then be obtained from the immune material, by a number of methods which are well known in the art, for example, protein purification methods including, but not limited to, chromatography.

EXAMPLE 6

Methods of Preparing a Passive Vaccine and Methods of Vaccinating an Organism with the Vaccine A passive vaccine is one which already contains an antibody or antibodies against a particular epitope or epitopes, as opposed to an active vaccine, which attempts to stimulate the immune system to produce such antibodies. Passive vaccines can be prepared against an epitope of a first biological unit which is capable of interacting with a second biological unit, according to the following procedure. First, at least one antibody which binds at least one epitope of the first biological unit is detected, as described above in Example 5. Optionally, such an antibody can also be obtained according to the methods given in Example 5.

Next, the antibody is placed in a vaccine carrier, according to Example 4. Examples of organisms to which such a vaccine could be administered include, but are not limited to, those given in Example 4.

EXAMPLE 7

A Diagnostic Tool for Detecting an Organism by Using a Representation

Frequently it is desirable to diagnose the presence of an immune response to a particular organism in a tissue or blood sample, or even in vivo. Such detection can be accomplished by using a representation of a single biological unit which could be an epitope of the organism of interest, for example, then putting the immune material which includes at least one antibody, such as the blood or tissue sample, in contact with the representation, and then using a detection assay to detect antibody binding to the representation. It should be noted that the representation must either be a peptide, or must cause a peptide to be displayed, for example on a coat protein of a phage. In any case, in the following description, when a representation is described as being bound by an antibody, for example, it is meant that a peptide is being bound by the antibody.

A diagnostic tool which can perform such a diagnosis has many potential biomedical uses, including the detection of organisms including, but not limited to viruses including but not limited to retrovirus species such as HIV and HTLV, hepatitis species such as Hepatitis A and Hepatitis B, influenza species, human papillomavirus, herpes species such as herpes simplex, RSV (respiratory syncytial virus) and cytomegalovirus; bacteria including, but not limited to, *Mycobacterium tuberculosis,* salmonella, staphylococcus species such as *Staph. aureus,* and shigella; parasites including, but not limited to, plasmodium species such as *Plasmodium falciparum,* leishmania species such as *Leishmania* major and *L. braziliensis braziliensis,* entamoeba species, giardia species, trichomonas species and trypanosoma species; and yeasts including, but not limited to, *Candida albicans.* Certainly, such diagnostic tools are known for detecting the presence of HIV for example. However, these tools do not rely upon the use of representations to detect the presence of an antibody which binds an epitope of an organism.

A novel diagnostic tool can be constructed from a representation of a single biological unit of the organism of interest, and a detection assay for determining when an antibody is actually bound to the representation. The representation is prepared according to one of the methods of Example 3. These detection assays can employ a detection moiety attached to the representation, a density gradient, or a chromatograph. Such a detection moiety can include fluorescent dyes such as rhodamine or fluorescein. These dyes can be detected by a spectrophotometer, for example.

Density gradients are well known in the art, and are prepared in the following manner. First, a density gradient is prepared by layering materials of different densities within a container, such as a tube. The material with the highest density is substantially near the bottom of the container, while the material with the lowest density is substantially near the top of the container. An example of such a material is a sucrose solution with varying concentrations of sucrose. The higher the concentration of sucrose, the higher the density of the solution.

After the density gradient has been prepared, a solution containing the representation and antibody or antibodies of interest is placed on top of the material with the lowest density, being careful not to disturb the gradient. The container with the density gradient is then subjected to ultracentrifugation. A representation which has been bound by an antibody will have a different density, and hence will move to a different layer, as compared to a representation which has not been bound by such an antibody. Therefore, each will migrate to a different position along the gradient. After ultracentrifugation, the location of the representation within the gradient can be detected according to methods which are well known in the art.

Yet another example of a detection assay employs a chromatograph. A chromatograph is a device for separating proteins according to some property. For example, proteins can be separated according to their relative solubility by thin-layer chromatography. In this procedure, a sample which includes proteins in solution is applied to a thin layer of absorbent material, such as cellulose or silica gel, which has been attached to a sheet of stiff material such as plastic or glass. At least one solvent is introduced to one edge of the absorbent material. As the solvent front moves through the absorbent material, the proteins are separated according to their relative solubility in the solvent. Alternatively, proteins can be separated by column chromatography, in which a sample which includes proteins in solution is applied to one end of a column containing a porous solid. Such a porous solid then separates the proteins by size, or by some other property. Clearly, any of these chromatographs could be used to separate a representation which is bound by an antibody of interest from a representation which is not so bound.

Thus, this diagnostic tool could be used as follows. First, the representation, is incubated with a sample containing an antibody. A sample is simply defined as containing an antibody, including, but not limited to, a portion of tissue or blood and immune material. "Incubated" is simply defined as allowing the sample to come in contact with the representation under conditions which are appropriate for permitting the binding of the antibody to the representation. For example, an appropriate buffer or buffers could be included, and the sample and representation could be maintained at an appropriate temperature. Next, the detection assay, as described above, could be performed to determine when the representation is bound by the antibody.

EXAMPLE 8

A Diagnostic Tool for Detecting a First Biological Unit which is Capable of Interacting with a Second Biological Unit by Using an Antibody Frequently it is desirable to diagnose the presence of a particular biological unit, including but not limited to an organism, in a tissue or blood sample, or even in vivo. Such detection can be accomplished by using an antibody or antibodies which bind to at least one epitope of the biological unit of interest, herein referred to as the "first biological unit". Next, a detection assay is used to detect antibody binding. A diagnostic tool which can perform such a diagnosis has many potential biomedical uses, including the detection of organisms including, but not limited to those organisms listed in the previous Examples. Other potential uses include the detection of both natural and artificial toxins, including but not limited to snake, insect and spider venom toxins, plant toxins and synthetic toxins. Such diagnostic tools are known for detecting the presence of HIV, for example. However, these tools generally do not rely upon antibodies which have been specifically prepared to bind an epitope which is involved in the interaction of two biological units. Certainly, such tools are not generally known for the detection of non-peptidic substances.

A novel diagnostic tool can be constructed from an antibody for binding at least epitope of a first biological unit which is capable of interacting with a second biological unit, and a detection assay for determining when the antibody is actually bound to the epitope. The antibody is prepared according to Example 5. The detection assay can employ a detection moiety attached to the antibody, a density gradient, or a chromatograph, for example. Such a detection moiety can include fluorescent dyes such as rhodamine or fluorescein. These dyes can be detected by a spectrophotometer, for example.

Density gradients are well known in the art, and are prepared in the following manner. First, a density gradient is prepared by layering materials of different densities within a container, such as a tube. The material with the highest density is substantially near the bottom of the container, while the material with the lowest density is substantially near the top of the container. An example of such a material is a sucrose solution with varying concentrations of sucrose. The higher the concentration of sucrose, the higher the density of the solution.

After the density gradient has been prepared, a solution containing the antibody or antibodies of interest is placed on top of the material with the lowest density, being careful not to disturb the gradient. The container with the density gradient is then subjected to ultracentrifugation. An antibody which has bound an epitope will have a different density, and hence will move to a different layer, as compared to an antibody which has not bound such an epitope. Therefore, each will migrate to a different position along the gradient. After ultracentrifugation, the location of the antibody within the gradient can be detected according to methods which are well known in the art.

Yet another example of a detection assay employs a chromatograph. A chromatograph is a device for separating proteins according to some property. For example, proteins can be separated according to their relative solubility by thin-layer chromatography. In this procedure, a sample which includes proteins in solution is applied to a thin layer of absorbent material, such as cellulose or silica gel, which has been attached to a sheet of stiff material such as plastic or glass. At least one solvent is introduced to one edge of the absorbent material. As the solvent front moves through the absorbent material, the proteins are separated according to their relative solubility in the solvent. Alternatively, proteins can be separated by column chromatography, in which a sample which includes proteins in solution is applied to one end of a column containing a porous solid. Such a porous solid then separates the proteins by size, or by some other property. Clearly, any of these chromatographs could be used to separate an antibody which is bound to an epitope of interest from an antibody which is not so bound.

This diagnostic tool could be used as follows. First, the antibody could be incubated with a sample containing a first biological unit of the organism of interest. A sample is simply defined as containing at least one first biological unit of the organism, including, but not limited to, a portion of tissue or blood and immune material. "Incubated" is simply defined as allowing the sample to come in contact with the at least one first biological unit under conditions which are appropriate for permitting the binding of the antibody to the at least one first biological unit. For example, an appropriate buffer or buffers could be included, and the sample and antibody could be maintained at an appropriate temperature. Next, the detection assay is used for determining when the antibody is bound to the at least one first biological unit of the organism.

While the invention has been described with respect to a limited number of embodiments, it will be appreciated that many variations, modifications and other applications of the invention may be made.

What is claimed is:

1. A method of preparing a bimolecular interaction library for a first biological unit and for a second biological unit, each biological unit having a discrete biological function, each of the first and second biological units having a genetic material, the genetic material being DNA or RNA coding for at least one peptide representing the biological unit, the genetic material having a fragment, and the fragment coding for at least one peptide, the method comprising the steps of:

(a) preparing a first fragment from the genetic material of the first biological unit;
   (b) preparing a first phage library having a first selection marker with said first fragment, such that a first peptide is displayed by said first phage library;
   (c) preparing a second fragment from the genetic material of the second biological unit;
   (d) preparing a second phage library having a second selection marker with said second fragment, such that a second peptide is displayed by said second phage library;
   (e) mixing said first phage library and said second phage library; and
   (f) co-selecting co-selected phages from said first phage library and from said second phage library by said first selection marker and said second selection marker when a selection process yields a positive result, such that said selection process yields said positive result only when said first peptide and said second peptide interact, and such that the bimolecular interaction library is formed from said co-selected phages.

2. The method of claim 1, wherein step (a) is performed by at least partially digesting the genetic material of the first biological unit and step (c) is performed by at least partially digesting the genetic material of the second biological unit.

3. The method of claim 2, wherein step (a) is performed by completely digesting the genetic material of the first biological unit and step (c) is performed by completely digesting the genetic material of the second biological unit.

4. The method of claim 3, wherein the genetic material of at least one of the first and the second biological units is a complete genome of an organism.

5. The method of claim 1, wherein step (a) comprises the steps of:
   (i) at least partially digesting the genetic material of the first biological unit to form a plurality of fragments;
   (ii) ligating said plurality of fragments to form at least one ligated fragment; and
   (iii) at least partially digesting said ligated fragment to form said first fragment.

6. The method of claim 5, wherein step (c) is performed by at least partially digesting the genetic material of the second biological unit to form said second fragment.

7. The method of claim 1, wherein step (c) comprises the steps of:
   (i) at least partially digesting the genetic material of the second biological unit to form a plurality of fragments;
   (ii) ligating said plurality of fragments to form at least one ligated fragment; and
   (iii) at least partially digesting said ligated fragment to form said second fragment.

8. The method of claim 7, wherein step (a) is performed by at least partially digesting the genetic material of the first biological unit to form said first fragment.

9. The method of claim 1, wherein each of the first and the second biological units is separately selected from the group consisting of a protein, a plurality of interacting proteins, and an epitope of a protein.

10. The method of claim 1, wherein at least one of the first and the second biological units is a non-protein structure mimicked by a mimotope.

11. The method of claim 1, wherein each of said first and said second fragments is cloned into a phage gene coding for a coat protein, such that said each of said first and said second peptides is displayed by said coat protein.

12. The method of claim 11, wherein said phage library has a filamentous phages and said coat protein is selected from the group consisting of pIII and pVIII.

13. The method of claim 1, wherein said first selection marker is an antibiotic-resistance gene and said second selection marker is infectivity.

14. The method of claim 1, wherein said first selection marker is a first fluorescent dye having a first emission spectrum and said second selection marker is a second fluorescent dye having a second emission spectrum, said first and said second spectra combining to form a third emission spectrum.

15. The method of claim 1, wherein said first selection marker is said first peptide and said second selection marker is said second peptide, such that said co-selected phages co-selected from said first library and from said second library have a characteristic selected from the group consisting of density, size and charge.

16. A bimolecular interaction library for a first biological unit and for a second biological unit, each biological unit having a discrete biological function, comprising a bimolecular interaction library prepared according to the method of claim 1.

17. A method for obtaining a bimolecular interaction combination of a first biological unit of a second biological unit, each biological unit having a discrete biological function, each of the first and the second biological units having genetic material, the genetic material being DNA or RNA coding for at least one peptide representing the biological unit, the genetic material having a fragment, and the fragment coding for at least one peptide, the method comprising the steps of:

(a) preparing a first fragment from the genetic material of the first biological unit;

(b) preparing a first phage library having a first selection marker with said first fragment, such that a first peptide is displayed by said first phage library;

(c) preparing a second fragment from the genetic material of the second biological unit;

(d) preparing a second phage library having a second selection marker with said second fragment, such that a second peptide is displayed by said second phage library;

(e) mixing said first phage library and said second phage library;

(f) co-selecting co-selected phages from said first phage library and from said second phage library by said first selection marker and said second selection marker when a selection process yields a positive result, such that said selection process yields said positive result only when said first peptide and said second peptide interact, and such that the bimolecular interaction library is formed from said co-selected phages; and (g) obtaining a first peptidic unit of said first peptide and a second peptidic unit of said second peptide, said first peptidic unit and said second peptidic unit forming the bimolecular interaction combination.

18. The method of claim 17, wherein said first and said second peptidic units are said first and said second peptides.

19. The method of claim 17, wherein said first and said second peptidic units are said first and said second fragments.

20. The method of claim 17, wherein step (a) is performed by at least partially digesting the genetic material of the first biological unit and step (c) is performed by at least partially digesting the genetic material of the second biological unit.

21. The method of claim 17, wherein step (a) is performed by completely digesting the genetic material of the first biological unit and step (c) is performed by completely digesting the genetic material of the second biological unit.

22. The method of claim 21, wherein the genetic material of at least one of the first and the second biological units is a complete genome of an organism.

23. The method of claim 17, wherein step (a) comprises the steps of:

(i) at least partially digesting the genetic material of the first biological unit to form a plurality of fragments;

(ii) ligating said plurality of fragments to form at least one ligated fragment; and (iii) at least partially digesting said ligated fragment to form said first fragment.

24. The method of claim 23, wherein step (c) is performed by at least partially digesting the genetic material of the second biological unit to form said second fragment.

25. The method of claim 17, wherein step (c) comprises the steps of:

(i) at least partially digesting the genetic material of the second biological unit to form a plurality of fragments;

(ii) ligating said plurality of fragments to form at least one ligated fragment; and (iii) at least partially digesting said ligated fragment to form said second fragment.

26. The method of claim 25, wherein step (a) is performed by at least partially digesting the genetic material of the first biological unit to form said first fragment.

27. The method of claim 17, wherein each of the first and the second biological units is separately selected from the group consisting of a protein, a plurality of interacting proteins, and an epitope of a protein.

28. The method of claim 17, wherein at least one of the first and the second biological units is a non-protein structure mimicked by a mimotope.

29. The method of claim 17, wherein each of said first and said second fragments is cloned into a phage gene coding for a coat protein, such that said each of said first and said second peptides is displayed by said coat protein.

30. The method of claim 29, wherein said phage library has filamentous phages and said coat protein is selected from the group consisting of pIII and pVIII.

31. The method of claim 17, wherein said first selection marker is an antibiotic-resistance gene and said second selection marker is infectivity.

32. The method of claim 17, wherein said first selection marker is a first fluorescent dye having a first emission spectrum and said second selection marker is a second fluorescent dye having a second emission spectrum, said first and said second spectra combining to form a third emission spectrum.

33. The method of claim 17, wherein said first selection marker is said first peptide and said second selection marker is said second peptide, such that said co-selected phages co-selected from said first library and from said second library have a characteristic selected from the group consisting of density, size and charge.

34. A bimolecular interaction combination of a first biological unit and of a second biological unit, each biological unit having a discrete biological function, each of the first and the second biological units having genetic material, the genetic material being DNA or RNA coding for at least one peptide representing the biological unit, the genetic material having a fragment, and the fragment coding for at least one peptide, comprising a bimolecular interaction combination prepared according to the method of claim 17.

* * * * *